United States Patent [19]

Pallett et al.

[11] Patent Number: 6,069,115
[45] Date of Patent: May 30, 2000

[54] METHOD OF CONTROLLING WEEDS IN TRANSGENIC CROPS

[75] Inventors: Ken Pallett, Ongar, United Kingdom; Richard Derose, Lyons, France; Bernard Pelissier, St Didier Au Mont d'Or, France; Alain Sailland, Lyons, France; Thomas Edward Vrabel, Raleigh, N.C.

[73] Assignee: Rhone-Poulenc Agrochimie, Lyons, France

[21] Appl. No.: 08/969,032

[22] Filed: Nov. 12, 1997

[51] Int. Cl.⁷ .............................. A01G 1/00; A01G 7/00; A01G 13/00
[52] U.S. Cl. ..................... 504/270; 548/248; 800/298; 504/116; 504/118
[58] Field of Search ................... 504/270, 116, 504/118; 548/248; 800/205, 200, 298

[56] References Cited

U.S. PATENT DOCUMENTS

| | | | |
|---|---|---|---|
| 5,188,642 | 2/1993 | Shah et al. | 800/205 |
| 5,374,606 | 12/1994 | Cramp et al. | 504/270 |

FOREIGN PATENT DOCUMENTS

| | | |
|---|---|---|
| WO98/02562 | 1/1998 | WIPO. |
| WO98/20144 | 1/1998 | WIPO. |
| WO98/51153 | 11/1998 | WIPO. |

OTHER PUBLICATIONS

Mazur et al Annu. Rev.Plant Physiol. Plant Mol. Biol. 40:441–470, 1989.
XP–002097551 Abstract, S.E.Curvay et al., Corn no–till weed control with preemergence RPA 201772, Re.Rep-.North.Cent.Weed Sci.Soc., vol. 53, 1996 pp. 438–440.

*Primary Examiner*—Lynette R. F. Smith
*Assistant Examiner*—Thomas Haas
*Attorney, Agent, or Firm*—Connolly Bove Lodge & Hutz LLP

[57] ABSTRACT

The invention relates to a method for the control of weeds at a crop locus, said method comprising the application of an effective amount of:

(a) a glyphosate herbicide which is glyphosate or a derivative thereof; and
(b) at least one HPPD-inhibiting herbicide;
  wherein the crop is tolerant to glyphosate and optionally the HPPD-inhibiting herbicide.

24 Claims, No Drawings

METHOD OF CONTROLLING WEEDS IN TRANSGENIC CROPS

BACKGROUND OF THE INVENTION

This invention relates to compositions comprising the use of a 5-enol pyruvyl shikimate-3-phosphonate synthase-inhibiting herbicide (such as glyphosate) and a p-hydroxyphenylpyruvate dioxygenase-inhibiting herbicide, and to their use on transgenic crops, in particular corn (*Zea mays*) and soybean.

DISCUSSION OR RELATED ART

Inhibitors of the enzyme p-hydroxyphenylpyruvate dioxygenase (HPPD) are discussed in a number of papers (Prisbyllu et al, Proc. Brighton Crop Prot. Vol. 2, (1993). pp731–738; Schulz el al., FEBS Letters, No. 2 (1993), Vol. 2, 162–166; Pallett et al, Pestic. Sci., Vol. 50 (1997) pages 83–84; and Lee et al, Weed Science Vol. 45 (1997) pages 601–609). HPPD-inhibiting herbicides are known in the literature, for example pyrazolate-type herbicides; 4-benzoylisoxazole herbicides (e.g. 5-cyclopropyl-4-(2-methylsulfonyl-4-trifluoromethylbenzoyl)isoxazole, known by the common name isoxaflutole), and 2-benzoylcyclohexane-1,3-dione herbicides [e.g. 2-(2-chloro-4-methylsulfonylbenzoyl)-cyclohexane-1,3-dione, known by the common name sulcotrione; and 2-(2'-nitro-4'-methylsulfonylbenzoyl)cyclohexane-1,3-dione]. These compounds possess good levels of weed control, However, under certain conditions, (e.g. where high levels of weed infestation exist and it is desirable to use higher dose rate of the compounds; or where the compounds are to be applied post-emergence) there can be a problem with the selectivity of these compounds in the presence of crops, for example soybeans or maize.

Herbicides inhibiting 5-enol pyruvylshikimate-3-phosphonate synthase (EPSPS) are well known as highly effective foliar herbicides. The most well known herbicide of this class of herbicide is glyphosate [N-(phosphonomethyl)glycine]. Glyphosate lacks selectivity in crop species and has therefore been used under conditions where there is no need for selectivity (e.g. as a total herbicide) or under conditions where there is no growing crop foliage present (e.g. burn-down/no-till).

An alternative approach to the above limitations is to use the above compounds in the presence of crops which have been genetically modified to provide enhanced tolerance to the compounds. For example U.S. Pat. Nos. 4,535,060; 4,769,061; 5,633,435; 5,627,061; 4,940,835; relate to the modification of crops to confer tolerance to EPSPS-inhibiting (e.g. glyphosate) herbicides. WO96/38567 describes transgenic crops having enhanced tolerance to HPPD-inhibiting compounds.

The increased use of EPSPS tolerant plants, for example in the Round-up Ready™ corn and soybean seeds now available has allowed farmers to apply glyphosate in areas where the crop is growing, without causing unacceptable levels of damage to the crop.

The combination of isoxaflutole and glyphosate is known for the use in burn-down/no-till control. However, this is applied in an area where the crop has not emerged and thus selectivity is not a necessary requirement, and further treatments of the field may be needed by the farmer using selective herbicides after sowing the seed to remove weeds which emerge after the application of the herbicide. This requires additional time and expense on the part of the farmer.

An object of the invention is to provide a single treatment to control weeds present at a crop locus.

A further object of the invention is to provide a method which maximises crop yield.

A still further object of the invention is to provide a method which allows the farmer to avoid applying unnecessary treatments of herbicide before the emergence of weeds, which allows the farmer maximum flexibility in deciding on a treatment programme.

These and other objects will become apparent from the following description, which are achieved in whole or in part by the present invention.

SUMMARY OF THE INVENTION

The present invention provides a method for the control of weeds at a crop locus, said method comprising the application of an effective amount of:
(a) a glyphosate herbicide which is glyphosate or a derivative thereof; and
(b) at least one HPPD-inhibiting herbicide;
wherein the crop locus comprises a crop tolerant to said glyphosate herbicide.

DESCRIPTION OF PREFERRED EMBODIMENTS

Preferably the transgenic crop is tolerant to glyphosate and said least one HPPD-inhibiting herbicide at the doses used.

Generally the herbicides are applied post-emergence of the crop, preferably early-post emergence. By the term "early post emergence" is meant the first four weeks after emergence of the crop. The application of the combination of the invention is preferably made two weeks after emergence of the crop. This period is very important in influencing the final yield potential of the crop. Typically, during the early post-emergent period when the crop is maize, the crop height is less than about 15 cm (preferably less than about 10 cm) and the weed height is less than about 10 cm (preferably less than about 5 cm).

The application of (a) and (b) is preferably made early post-emergence as this allows the control of late-germinating weeds to be accomplished without the need to apply a second application of the glyphosate herbicide which, while effective in controlling weeds which have emerged at the time of their application, generally do not control weeds which have protracted germinating periods (due to the lack of residual activity in these compounds) and thus need to be applied again late-post emergence. The HPPD-inhibiting herbicide provides a residual activity. Furthermore, the use of an HPPD-inhibiting herbicide in combination with glyphosate also lessens the risk of weed population shifts, due to increasing application of a single herbicide over successive seasons.

Weeds that may be controlled by the method of the invention include grass weeds, broad-leaf weeds and sedges. The method of the invention is particularly useful in controlling certain needs which glyphosate may not fully control, in particular waterhemp (Amaranthus spp), nightshades and velvetleaf (*Abutilon theophrasti*).

Examples of grass weeds include *Alopecurus myosuroides, Avena fatua, Digitaria sanguinalis, Echinochloa crus-galli, Sorghum bicolor, Eleusine indica* and *Setaria* spp, e.g. *Setaria faberii* or *Setaria viridis*.

Examples of broad-leaf weeds include *Abutilon theophrasti, Amaranthus retroflexus, Bidens pilosa, Che-*

*nopodium album, Galium aparine,* Ipomoea spp, e.g. *Ipomoea purpurea, Sesbanta exaltata, Sinapis arvensis, Solanum nigrum* and *Xanthium strumarium.*

An example of a sedge includes *Cyperus esculentus.*

The crop species which may be used in the method of the invention include maize, sugarcane, soybean, cotton, canola, clover, sugar beet, grain sorghum, peas, beans, potatoes, peanuts, wheat and barley. Preferred crops include maize, sugarcane, soybean, cotton, canola and clover. Particularly preferred crop species are maize and soybean, especially maize.

Preferably the crop contains a gene which encodes class II EPSPS enzyme.

Crops possessing enhanced tolerance to both glyphosate herbicides and HPPD-inhibiting herbicides are described in PCT application No. PCT/FR97/01256, which was filed before the present application but was unpublished at the date of filing.

In general the application rate of the glyphosate herbicide is from about 400 to about 1200 g acid equivalent (a.e.)/ha, preferably from about 500 g/ha to about 800 g a.e./ha; and the application rate of the HPPD-inhibiting herbicide is generally from about 20 g/ha to about 500 g/ha, preferably from about 40 g/ha to about 150 g/ha. It will be understood that the application rates used will depend on the growth stage of the weeds, the climatic conditions, the time of application, the type of weeds present, the crops and other parameters apparent to the skilled worker.

The glyphosate herbicide may be applied in its acid form or as a derivative thereof, such as the mono isopropylammonium salt, the sodium salt, trimesium salt (sulfosate) or a mixture thereof. Preferably the mono isopropylammonium salt is used.

Preferably the weight ratio of (a):(b) is from about 0.8:1 to about 60:1, more preferably from about 3.3:1 to about 20:1.

In one preferred aspect of the present invention the HPPD-inhibiting herbicide is a 4-benzoylisoxazole herbicide, preferably having the general formula(I):

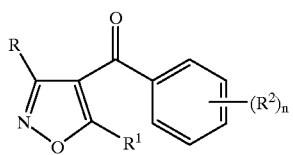

(I)

wherein R is hydrogen or —CO$_2$R$^3$;

R$^1$ is C$_{1-4}$ alkyl or C$_{3-6}$ cycloalkyl optionally substituted by C$_{1-6}$ alkyl;

R$^2$ is selected from halogen, nitro, cyano, —S(O)$_p$R$^6$, —(CR$^4$R$^5$)$_q$S(O)$_p$R$^6$, —N(R$^7$)SO$_2$R$^6$, C$_{1-6}$ alkoxy, —OSO$_2$R$^6$, C$_{1-4}$ haloalkoxy, C$_{1-4}$ alkyl and C$_{1-4}$ haloalkyl;

or two groups R$^2$, on adjacent carbon atoms of the phenyl ring may, together with the carbon atoms to which they are attached, form a 5 or 6 membered saturated or unsaturated heterocyclic ring containing up to three ring heteroatoms selected from nitrogen, oxygen and sulfur, which ring may be optionally substituted by one or more groups selected from halogen, nitro, —S(O)$_p$ R$^6$, C$_{1-4}$ alkyl, C$_{1-4}$ alkoxy, C$_{1-4}$ haloalkyl and C$_{1-4}$ haloalkoxy, it being understood that a sulphur atom, where present in the ring, may be in the form of a group —SO— or —SO$_2$—;

n is an integer from one to five; p is zero, one or two;

q is one or two; where q is two the groups (CR$^4$R$^5$) may be the same or different;

R$^3$ is C$_{1-4}$ alkyl;

R$^4$ and R$^5$ are independently hydrogen or C$_{1-4}$ alkyl;

R$^6$ is C$_{1-4}$ alkyl, or phenyl or benzyl, each of phenyl and benzyl optionally bearing from one to five substituents which may be the same or different selected from the group consisting of halogen, C$_{1-4}$ alkyl, C$_{1-4}$ alkoxy, C$_{1-4}$ haloalkyl, C$_{1-4}$ haloalkoxy, nitro and —S(O)$_p$CH$_3$;

and R$^7$ is hydrogen or C$_{1-6}$ alkyl;

or an agriculturally acceptable salt thereof.

In this description the term "agriculturally acceptable salts" means salts the cations or anions of which are known and accepted in the art for the formation of salts for agricultural or horticultural use. Preferably the salts are water-soluble. Suitable salts with bases include alkali metal (eg. sodium and potassium), alkaline earth metal (eg. calcium and magnesium), ammonium and amine (eg. diethanolamine, triethanolamine, octylamine, morpholine and dioctylmethylamine) salts. Suitable acid addition salts, formed by compounds of formula (I) containing an nitrogen atom with an available lone pair, include salts with inorganic acids, for example hydrochlorides, sulphates, phosphates and nitrates and salts with organic acids, for example acetic acid, It will be understood that in certain cases the groups R$^1$, R$^2$, R$^3$, R$^4$, R$^5$, R$^6$ and R$^7$ may give rise to stereoisomers and geometric isomers. All such forms are embraced by the present invention.

Throughout this description the terms "alkyl" and "alkoxy" refer to straight or branched chains. The terms "haloalkyl" and "haloalkoxy" refer to alkyl and alkoxy respectively each substituted by at least one halogen. The term "halogen" refers to fluorine, chlorine, bromine and iodine.

In formula (I) above, preferably R is hydrogen or —CO$_2$CH$_2$CH$_3$.

In formula (I) above, preferably n is two or three. R$^1$is preferably cyclopropyl.

Compounds of formula (I) in which either n is three and the groups (R$^2$)$_n$ occupy the 2.3 and 4-positions of the benzoyl ring; or in which n is two and the groups (R$^2$)$_n$ occupy the 2 and 4- positions of the benzoyl ring; are preferred.

In formula (I) above, R$^2$ is preferably selected from halogen (preferably chlorine or bromine), —S(O)$_p$Me, trifluoromethyl, C$_{1-4}$ haloalkoxy, C$_{1-4}$ alkoxy and —CH$_2$S (O)$_p$Me.

In formula (I) above, preferably one of the groups R$^2$ is —S(O)$_p$Me.

Compounds of formula (I) of particular interest include 5-cyclopropyl-4-(2-methylsulphonyl-4-trifluoromethyl) benzoylisoxazole; 4-(2-chloro-4-methylsulphonyl)benzoyl-5-cyclopropylisoxazole; 4-(4-chloro-2-methylsulphonyl) benzoyl-5-cyclopropylisoxazole; 4-(4-bromo-2-methylsulphonyl)benzoyl-5-cyclopropylisoxazole, ethyl 5-cyclopropyl-4-(2-methylsulphonyl-4-trifluoromethyl) benzoylisoxazole-3-carboxylate; 4-[4-bromo-2-(methylsulphonylmethyl)benzoyl]-5-cyclopropylisoxazole; 4-[4-bromo-3-(2,2-difluoroethoxy)-2-methylsulphonyl-benzoyl]-5-cyclopropylisoxazole; 5-cyclopropyl-4-[2,2-difluoro-4-(methanesulphonylmethyl)-1,3-benzodioxol-5-oyl]isoxazole and 5-cyclopropyl-4-(4-fluoro-3-methoxy-2-methylsulphonylbenzoyl)isoxazole. Most preferably the compound of formula (I) is 5-cyclopropyl-4-(2- methylsulphonyl-4-trifluoromethyl)benzoylisoxazole or 5-cyclopropyl-4(4-fluoro-3-methoxy-2-methylsulphonylbenzoyl)isoxazole.

Herbicidal 4-benzoylisoxazoles are known from EP418175, EP487357, EP527036, EP560482, WO94/14782, and U.S. Pat. Nos. 5,371,064; 5,371,063; 5,371,064; 5,489,570 and 5,656,573.

Where the HPPD-inhibiting is a 4-benzoylisoxazole, it is generally applied at an application rate from about 20 g/ha to about 500 g/ha, preferably from about 40 g/ha to about 150 g/ha, more preferably from about 60 g/ha to about 80 g/ha.

It has unexpectedly been found that in certain cases where the HPPD-inhibiting herbicide is a 4-benzoylisoxazole the combinations of the present invention provide a synergistic level of control of one or more weed species and in a further preferred feature of the present invention there is provided a synergistic herbicidal composition comprising a compound of formula (I) above and a glyphosate herbicide which is glyphosate or a derivative thereof, in association with a agriculturally acceptable diluent or carrier. Preferably the compound of formula (I) is 5-cyclopropyl-4-(4-fluoro-3-methoxy-2-methylsulphonylbenzoyl)isoxazole.

In another preferred aspect of the present invention the HPPD-inhibiting herbicide is a 2-benzoyl-cyclohexane-1,3-dione derivative, preferably having the general formula (II):

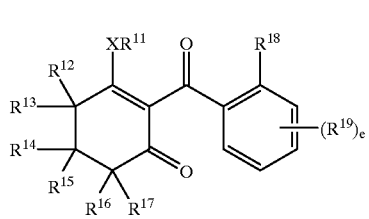

wherein
$R^{11}$ is hydrogen, $C_{1-6}$ alkyl, or phenyl;
X is oxygen or $-S(O))_z$ where z is zero, one or two;
$R^{12}$, $R^{13}$, $R^{14}$, $R^{15}$ $R^{16}$ and $R^{17}$ independently represent hydrogen or $C_{1-6}$ alkyl;
or $R^{12}$ and $R^{14}$, together with the carbon atoms to which they are attached, form a three to five membered saturated carbocyclic ring; or $R^{12}$ and $R^{16}$ together form an ethylene radical;
$R^{18}$ is nitro, halogen, cyano, $C_{1-4}$ alkyl, $C_{1-4}$ haloalkyl, $C_{1-4}$ alkoxy, $C_{1-4}$ haloalkoxy or $-S(O)_zR^{20}$;
$R^{19}$ is halogen, nitro, cyano, $C_{1-4}$ alkyl, $C_{1-4}$ alkoxy, $C_{1-4}$ haloalkyl, $C_{1-4}$ haloalkoxy, $-NR^{21} R^{22}$, $-S(O)_zR^{23}$, $-OSO_2R^{23}$, $-(CR^{24}R^{25})_aS(O)_zR^{23}$ or $-NR^{26}SO_2R^{23}$,
e is an integer from one to four;
$R^{20}$ represents $C_{1-4}$ alkyl;
$R^{21}$, $R^{22}$, $R^{24}$, $R^{25}$ and $R^{26}$ independently represent hydrogen or $C_{1-4}$ alkyl;
$R^{23}$ is $C_{1-4}$ alkyl, phenyl or benzyl, each of phenyl and benzyl optionally bearing from one to five substituents which may be the same or different selected from the group consisting of halogen, $C_{1-4}$ alkyl, $C_{1-4}$ alkoxy, $C_{1-4}$ haloalkyl, $C_{1-4}$ haloalkoxy, nitro and $-S(O)_zCH_3$;
a is a one or two, where a is two the groups $(CR^{24}R^{25})$ may be the same or different.
an enolic tautomeric form thereof, or an agriculturally acceptable salt or metal complex thereof.

It will be understood that the compounds of formula (II) may exist in enolic tautomeric forms that may give rise to geometric isomers. Furthermore, in certain cases the groups $R^{11}$ to $R^{19}$ may give rise to stereoisomers and geometric isomers. All such forms are embraced by the present invention.

In this description by the term "metal complexes" is meant compounds in which one or both of the oxygen atoms forming part of a 1,3-dione [in formula (II) and (III)] act as chelating agents to a metal cation. Examples of such cations include zinc, manganese, cupric, cuprous, ferric, ferrous, titanium and aluminium. It will be understood that in the description that follows, reference to compounds of formula (II) or (III) includes agriculturally acceptable salts, metal complexes or enolic tautomeric forms thereof. Preferably the compounds of formula (II) may be provided in the form of a metal complex, in particular a transition metal complex, for example as described in International Patent Application No. WO97/277848.

Preferably $R^{11}$ is hydrogen and X is oxygen. Preferably $R^{12}$, $R^{13}$, $R^{16}$ and $R^{17}$ each represent hydrogen, and $R^{14}$ and $R^{15}$ independently represent hydrogen or methyl.

Preferably $R^{18}$ is halogen or nitro.

Preferably $R^{19}$ is $C_{1-4}$ alkoxy or $-S(O)_zR^{23}$ or $-OSO_2R^{23}$, where $R^{23}$ is $C_{1-4}$ alkyl. More preferably $R^{19}$ is ethoxy or $-S(O)_zR^{23}$, where $R^{23}$ is methyl or ethyl. Most preferably a group $R^{19}$ is $-SO_2CH_3$ and occupies the 4-position of the benzoyl ring.

e is preferably one or two. When e is one preferably $R^{19}$ occupies the 4-position of the benzoyl ring; when e is two preferably the two groups $R^{19}$ occupy the 3- and 4-positions of the benzoyl ring.

Preferably the compound of formula (II) is 2-(2-chloro-4-methylsulfonylbenzoyl)cyclohexane-1,3-dione (sulcotrione); 2-(2-nitro-4'-methylsulfonylbenzoyl)cyclohexane-1,3-dione; 2-(2'-nitro-4-methylsulfonylexybenzoyl)cyclohexane-1,3-dione; or 2-(2'-chloro-3-ethoxy-4'-ethylsulfonylbenzoyl)-4-methylcyclohexane-1,3-dione, or an agriculturally acceptable salt or metal complex thereof.

Compounds of formula (II) are known from U.S. Pat. No. 5,006,158; U.S. Pat. No. 4,780,127, U.S. Pat. No. 4,806,146, U.S. Pat. No. 4,946,981, WO9408988 and WO9404525, the contents of which are incorporated herein by reference and relied upon.

In yet another preferred aspect of the invention the HPPD-inhibiting herbicide is a 2-cyano-1,3-dione herbicide, preferably having the general formula (III):

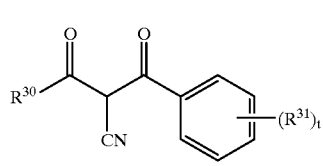

wherein $R^{30}$ is $C_{1-4}$ alkyl or $C_{3-6}$ cycloalkyl optionally substituted by $C_{1-6}$ alkyl;
$R^{31}$ is selected from halogen, nitro, cyano, $-S(O)_rR^{32}$, $-(CR^{33}R^{34})_sS(O)_rR^{32}$, $-N(R^{35})SO_2R^{32}$, $C_{1-6}$ alkoxy, $-OSO_2R^{32}$, $C_{1-4}$ haloalkoxy, $C_{1-4}$ alkyl and $C_{1-4}$ haloalkyl.
or two groups $R^{31}$, on adjacent carbon atoms of the phenyl ring may, together with the carbon atoms to which they are attached, form a 5 or 6 membered saturated or unsaturated heterocyclic ring containing up to three ring heteroatoms selected from nitrogen, oxygen and sulfur, which ring may be optionally substituted by one or more groups selected from halogen, nitro, $-S(O)_r$ $R^{32}$, $C_{1-4}$ alkyl, $C_{1-4}$ alkoxy, $C_{1-4}$ haloalkyl and $C_{1-4}$ haloalkoxy, it being understood that a sulphur atom, where present in the ring, may be in the form of a group —SO— or —SO$_2$—;

t is an integer from one to five (preferably one, two or three);

r is zero, one or two;

$R^{32}$ is $C_{1-4}$ alkyl, or phenyl or benzyl, each of phenyl and benzyl optionally bearing from one to five substituents which may be the same or different selected from the group consisting of halogen, $C_{1-4}$ alkyl, $C_{1-4}$ alkoxy, $C_{1-4}$ haloalkyl, $C_{1-4}$ haloalkoxy, nitro and —S(O)$_r$CH$_3$;

$R^{33}$, $R^{34}$ and $R^{35}$ are independently hydrogen or $C_{1-4}$ alkyl;

v is one or two; where v is two the groups (CR$^{33}$R$^{34}$) may be the same or different;

an enolic tautomeric form thereof, or an agriculturally acceptable salt or metal complex thereof.

It will be understood that the compounds of formula (III) may exist in enolic tautomeric forms that may give use to geometric isomers around the enolic double bond. Furthermore, in certain cases the groups $R^{30}$ to $R^{32}$ may give rise to stereoisomers and geometric isomers. All such forms are embraced by the present invention.

$R^{30}$ is preferably 1-methylcyclopropyl or, most preferably cyclopropyl.

In formula (III) above, $R^{31}$ is preferably selected from halogen (preferably chlorine or bromine), —S(O)$_r$Me, trifluoromethyl, $C_{1-4}$ haloalkoxy, $C_{1-4}$ alkoxy and —CH$_2$S(O)$_r$Me.

In formula (III) above, preferably one of the groups $R^{31}$ is —S(O)$_r$Me.

Compounds of formula (III) of particular interest include 3-cyclopropyl-2-cyano-1-(2-methylsulphonyl-4-trifluoromethylphenyl)propan-1,3-dione; 1-(2-chloro-4-methylsulphonylphenyl)-2-cyano-3-cyclopropylpropan-1,3-dione; 2-cyano-3-cyclopropyl-1-(4-fluoro-3-methoxy-2-methylsulphonylphenyl)propan-1,3-dione; 2-cyano-1-(4-methylsulphonyl-2-trifluoromethylphenyl)-3-(1-methylcyclopropyl)propan-1,3-dione; and 1-(4-chloro-2-methylsulphonylphenyl)-2-cyano-3-cyclopropylpropan-1,3-dione.

Compounds of formula (I) in which either t is three and the groups (R$^2$)$_n$ occupy the 2.3 and 4-positions of the benzoyl ring; or in which t is two and the groups (R$^2$)$_n$ occupy the 2 and 4-positions of the benzoyl ring; are preferred.

Compounds of formula (III) are known from-n EP469630, EP469631 and EP560482, the contents of which are incorporated herein by reference and relied upon.

The following non-limiting example illustrates the invention.

EXAMPLE 1

The following experiment were conducted in Iowa and South Dakota with applications of 5-cyclopropyl-4-(4-fluoro-3-methoxy-2-methylsulphonylbenzoyl)isoxazole (hereafter referred to as the "isoxazole"; technical material formulated as a suspension concentrate containing 200 g/l active ingredient) and the isopropylamine salt of glyphosate (using the commercial formulation "Roundup Bioforce", registered trade mark, a soluble concentrate containing 360 g/l active ingredient plus adjuvants) alone or in tank mix combination. Roundup-Ready™ soybeans mere used in the trials, which is a glyphosate tolerant crop; the varieties used in Iowa were Pioneer 9211RR (P9211RR), Pioneer 9294RR (P9294RR); and the varieties used in S Dakota were DeKalb 266 (DEK266), DeKalb 296 (DEK296), Pioneer 9294 (P9294RR), Pioneer 9333 (P9333RR), Pioneer 9344 (P9344RR), K2626RR, and Pioneer 9363 (P9363RR). In Iowa the soil type was a silt loam; in South Dakota the soil was a loam.

The plots were drill-sown with weeds and the crop prior to application of the herbicides. The herbicides were applied along or in combination 18 and 20 days after sowing in South Dakota and Iowa respectively. At the time of application the weeds were between about 1.5 and about 6 inches tall (3.8 and 15.3 cm respectively) and the soybean was at the 2 leaf growth stage (about 4 to 6 inches tall, i.e. about 10 to 15 cms). In addition, weeds were also drilled just prior to planting (The same day as the application in S. Dakota and the previous day in Iowa) in order to determine whether the isoxazole was effective in controlling these weeds which emerged after the application of glyphosate. 2 Replicates were performed. Percentage phytotoxicity was assessed visually 26–28 days after treatment (DAT).

The following results were obtained. In the tables that follow the weeds are identified by their Bayer codes and the crops by the codes used above). The dose rates are given in grammes of active ingredient per hectare (g/ha) of the salt and the figures in parenthesis indicate the expected figure of control according to the Colby formula (Colby S. R., 1967, Weeds 15, 20–22). "First planting" refers to the weeds which had emerged at the time of application of the isoxazole and glyphosate. "Second planting" refers to the weeds which were sown just before the herbicides were applied.

TABLE 1

Iowa 28 DAT - First planting

| Compound | Dose Rate | ABUTH | AMARE | AMATA | IPOHE | SETFA | SETVI |
|---|---|---|---|---|---|---|---|
| isoxazole | 100 | 93 | 15 | 45 | 0 | 55 | 50 |
| glyphosate | 500 | 8 | 100 | 100 | 8 | 100 | 100 |
| isoxazole + | 100 + | 97 | 100 | 100 | 45 | 100 | 100 |
| glyphosate | 500 | (94) | (100) | (100) | (8) | (100) | (100) |
| isoxazole | 150 | 100 | 25 | 55 | 95 | 60 | 55 |
| glyphosate | 500 | 8 | 100 | 100 | 8 | 100 | 100 |
| isoxazole + | 150 + | 100 | 100 | 100 | 55 | 100 | 100 |
| glyphosate | 500 | (100) | (100) | (100) | (95) | (100) | (100) |

TABLE 2

Iowa 28 DAT - Second planting

| Compound | Dose Rate | ABUTH | AMARE | AMATA | IPOHE | SETFA | SETVI |
|---|---|---|---|---|---|---|---|
| isoxazole | 100 | 100 | 30 | 30 | 20 | 55 | 45 |
| glyphosate | 500 | 8 | 88 | 80 | 8 | 100 | 8 |
| isoxazole + | 100 + | 100 | 75 | 60 | 50 | 100 | 100 |
| glyphosate | 500 | (100) | (92) | (86) | (26) | (100) | (49) |
| isoxazole | 150 | 100 | 30 | 30 | 30 | 65 | 55 |
| glyphosate | 500 | 8 | 88 | 80 | 8 | 100 | 8 |
| isoxazole + | 150 + | 100 | 90 | 90 | 78 | 100 | 100 |
| glyphosate | 500 | (100) | (92) | (86) | (36) | (100) | (100) |

TABLE 3

S Dakota 26 DAT - First planting

| Compound | Dose Rate | ABUTH | AMARE | AMATA | CHEAL | HELAN | IPOSS | SETFA | SETGL | SETVI |
|---|---|---|---|---|---|---|---|---|---|---|
| isoxazole | 100 | 53 | 28 | 33 | 38 | 18 | 18 | 58 | 63 | 60 |
| glyphosate | 500 | 75 | 75 | 85 | 88 | 99 | 30 | 99 | 93 | 98 |
| isoxazole + | 100 + | 88 | 65 | 90 | 90 | 100 | 33 | 96 | 94 | 100 |
| glyphosate | 500 | (88) | (82) | (90) | (93) | (99) | (43) | (100) | (97) | (99) |
| isoxazole | 150 | 83 | 63 | 83 | 53 | 18 | 45 | 88 | 85 | 80 |
| glyphosate | 500 | 75 | 75 | 85 | 88 | 99 | 30 | 99 | 93 | 98 |
| isoxazole + | 150 + | 95 | 73 | 82 | 90 | 99 | 53 | 99 | 94 | 99 |
| glyphosate | 500 | (96) | (91) | (97) | (94) | (99) | (62) | (100) | (99) | (100) |

TABLE 4

S Dakota 26 DAT - Second planting

| Compound | Dose Rate | ABUTH | AMARE | AMATA | IPOSS | SETFA | SETGL | SETVI |
|---|---|---|---|---|---|---|---|---|
| isoxazole | 100 | 68 | 85 | 75 | 25 | 56 | 73 | 56 |
| glyphosate | 500 | 0 | 0 | 0 | 0 | 0 | 0 | 0 |
| isoxazole + | 100 + | 80 | 88 | 70 | 30 | 65 | 63 | 68 |
| glyphosate | 500 | (69) | (85) | (75) | (25) | (55) | (73) | (65) |
| isoxazole | 150 | 88 | 96 | 73 | 30 | 78 | 80 | 78 |
| glyphosate | 500 | 0 | 0 | 0 | 0 | 0 | 0 | 0 |
| isoxazole + | 150 + | 90 | 93 | 90 | 38 | 65 | 73 | 73 |
| glyphosate | 500 | (99) | (96) | (73) | (30) | (78) | (90) | (78) |

TABLE 5

Effect on soybean (27 DAT)

| Compound | Dose Rate | DEK266 | DEK296 | K2626RR | P9211RR | P9294RR | P9333RR | P9344RR | P9363RR | S2174RR |
|---|---|---|---|---|---|---|---|---|---|---|
| isoxazole | 100 | 0 | 0 | 0 | 0 | 0 | 0 | 0 | 0 | 0 |
| glyphosate | 500 | 0 | 0 | 0 | 0 | 0 | 0 | 0 | 0 | 0 |
| isoxazole + glyphosate | 100 + 500 | 10 | 10 | 0 | 0 | 4 | 10 | 10 | 10 | 0 |
| isoxazole | 150 | 0 | 0 | 0 | 0 | 0 | 0 | 0 | 0 | 0 |
| isoxazole + glyphosate | 150 + 500 | 2 | 2 | 0 | 0 | 1 | 2 | 2 | 2 | 0 |

Note:
ABUTH = *Abutilon theophrasti*
AMATA = *Amaranthus rudis*
CHEAL = *Chenopodium album*
HELAN = *Helianthus annus*
IPOSS = *Ipomoea purpurea*
SETFA = *Setaria faberii*
SETGL = *Setaria glauca*
SETVI = *Setaria viridis*
AMARA = *Amaranthus retroflexus*
IPOHE = *Ipomoea hederacea*

We claim:

1. A method for the control of weeds at a crop locus, which comprises a single post-emergent application to the crop locus of effective amounts of:
   a) a glyphosate herbicide or derivative thereof; and
   b) at least one HPPD-inhibiting herbicide selected from the group consisting of 4-benzoylisoxazoles, 2-benzoylcyclohexane-1,3-dione derivatives, and 2-cyano-1,3-diones;
   wherein the crop locus comprises a crop tolerant to said glyphosate herbicide.

2. A method according to claim 1 wherein the crop is tolerant to glyphosate and said HPPD-inhibiting herbicide.

3. A method according to claim 1 in which the crop is selected from maize, sugarcane, soybean, cotton, canola and clover.

4. A method according to claim 3 in which the crop is maize or soybean.

5. A method according to claim 4 in which the crop height is less than about 15 cm and the weed height is less than about 10 cm.

6. A method according to claim 1 in which the application rate of the glyphosate herbicide is from about 400 to about 1200 g acid equivalent (a.e)/ha.

7. A method according to claim 6 in which the application rate of the HPPD-inhibiting herbicide is from about 20 g/ha to about 500 g/ha.

8. A method according to claim 1 in which the weight ratio of (a):(b) is from about 0.8:1 to about 60:1.

9. A method according to claim 1 in which the glyphosate derivative is a salt selected from the mono isopropylammonium salt, the sodium salt and the trimesium salt.

10. A method according claim 1 in which the HPPD-inhibiting herbicide is a 4-benzoylisoxazole herbicide.

11. A method according to claim 10 in which the 4-benzoylisoxazole herbicide has the formula (I):

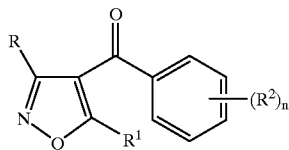

(I)

wherein R is hydrogen or $-CO_2R^3$;

$R^1$ is $C_{1-4}$ alkyl or $C_{3-6}$ cycloalkyl optionally substituted by $C_{1-6}$ alkyl;

$R^2$ is selected from halogen, nitro, cyano, $-S(O)_pR^6$, $-(CR^4R^5)_qS(O)_pR^6$, $-N(R^7)SO_2R^6$, $C_{1-6}$ alkoxy, $-OSO_2R^6$, $C_{1-4}$ haloalkoxy, $C_{1-4}$ alkyl and $C_{1-4}$ haloalkyl;

or two groups $R^2$, on adjacent carbon atoms of the phenyl ring may, together with the carbon atoms to which they are attached, form a 5 or 6 membered saturated or unsaturated heterocyclic ring containing up to three ring heteroatoms selected from nitrogen, oxygen and sulfur, which ring may be optionally substituted by one or more groups selected from halogen, nitro, $-S(O)_p$ $R^6$, $C_{1-4}$ alkyl, $C_{1-4}$ alkoxy, $C_{1-4}$ haloalkyl and $C_{1-4}$ haloalkoxy; it being understood that a sulphur atom, where present in the ring, may be in the form of a group $-SO-$ or $-SO_2-$;

n is an integer from one to five; p is zero, one or two;

q is one or two; where q is two the groups ($CR^4R^5$) may be the same or different $R^3$ is $C_{1-4}$ alkyl;

$R^4$ and $R^5$ are independently hydrogen or $C_{1-4}$ alkyl;

$R^6$ is $C_{1-4}$ alkyl, or phenyl or benzyl, each of phenyl and benzyl optionally bearing from one to five substituents which may be the same or different selected from the group consisting of halogen, $C_{1-4}$ alkyl, $C_{1-4}$ alkoxy, $C_{1-4}$ haloalkyl, $C_{1-4}$ haloalkoxy, nitro and $-S(O)_pCH_3$;

and $R^7$ is hydrogen or $C_{1-6}$ alkyl;

or an agriculturally acceptable salt thereof.

12. A method according to claim 11 having one or more of the following features:

R is hydrogen or $-CO_2CH_2CH_3$;

$R^1$ is cyclopropyl;

$R^2$ is halogen, $-S(O)_pMe$, trifluoromethyl, $C_{1-4}$ haloalkoxy, $C_{1-4}$ alkoxy or $-CH_2S(O)_pMe$;

n is two or three.

13. A method according to claim 12 in which either n is three and the groups ($R^2$)$_n$ occupy the 2,3 and 4-positions of the benzoyl ring; or n is two and the groups ($R^2$)$_n$ occupy the 2 and 4-positions of the benzoyl ring.

14. A method according to claim 11 in which the compound of formula (I) is 5-cyclopropyl-4-(2-methylsulphonyl-4-trifluoromethyl)benzoylisoxazole; 4-(2-chloro-4-methylsulphonyl)benzoyl-5-cyclopropylisoxazole; 4-(4-chloro-2-methylsulphonyl)benzoyl-5-cyclopropylisoxazole; 4-(4-bromo-2-methylsulphonyl)benzoyl-5-cyclopropylisoxazole; ethyl 5-cyclopropyl-4-(2-methylsulphonyl-4-trifluoromethyl)benzoylisoxazole-3-carboxylate; 4-[4-bromo-2-(methylsulphonylmethyl)benzoyl]-5-cyclopropylisoxazole; 4-[4-bromo-3-(2,2-difluoroethoxy)-2-methylsulphonylbenzoyl]-5-cyclopropylisoxazole; 5-cyclopropyl-4-[2,2-difluoro-4-(methanesulphonylmethyl)-1,3-benzodioxol-5-oyl] isoxazole and 5-cyclopropyl-4-(4-fluoro-3-methoxy-2-methylsulphonylbenzoyl)isoxazole.

15. A method according to claim 14 in which the compound of formula (I) is 5-cyclopropyl-4-(2-methylsulphonyl-4-trifluoromethyl)benzoylisoxazole or 5-cyclopropyl-4-(4-fluoro-3-methoxy-2-methylsulphonyl-benzoyl)isoxazole.

16. A method according to claim 1 in which the HPPD-inhibiting herbicide is a 2-benzoylcyclohexane-1,3-dione derivative.

17. A method according to claim 16 in which the 2-benzoyl-cyclohexane-1,3-dione derivative has the general formula (II):

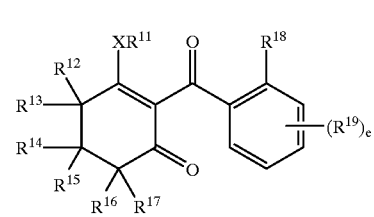

(II)

wherein $R^{11}$ is hydrogen, $C_{1-6}$ alkyl, or phenyl;

X is oxygen or —S(O)$_z$ where z is zero, one or two;

$R^{12}$, $R^{13}$, $R^{14}$, $R^{15}$, $R^{16}$ and $R^{17}$ independently represent hydrogen or $C_{1-6}$ alkyl;

or $R^{12}$ and $R^{14}$, together with the carbon atoms to which they are attached, form a three to five membered saturated carbocyclic ring; or $R^{12}$ and $R^{16}$ together form an ethylene radical;

$R^{18}$ is nitro, halogen, cyano, $C_{1-4}$ alkyl, $C_{1-4}$ haloalkyl, $C_{1-4}$ alkoxy, $C_{1-4}$ haloalkoxy or —S(O)$_z$R$^{20}$;

$R^{19}$ is halogen, nitro, cyano, $C_{1-4}$ alkyl, $C_{1-4}$ alkoxy, $C_{1-4}$ haloalkyl, $C_{1-4}$ haloalkoxy, —NR$^{21}$R$^{22}$, —S(O)$_z$R$^{23}$, —OSO$_2$R$^{23}$, —(CR$^{24}$R$^{25}$)$_a$S(O)$_z$R$^{23}$ or —NR$^{26}$SO$_2$R$^{23}$, e is an integer from one to four;

$R^{20}$ represents $C_{1-4}$ alkyl;

$R^{21}$, $R^{22}$, $R^{24}$, $R^{25}$ and $R^{26}$ independently represent hydrogen or $C_{1-4}$ alkyl;

$R^{23}$ is $C_{1-4}$ alkyl, phenyl or benzyl, each of phenyl and benzyl optionally bearing from one to five substituents which may be the same or different selected from the group consisting of halogen, $C_{1-4}$ alkyl, $C_{1-4}$ alkoxy, $C_{1-4}$ haloalkyl, $C_{1-4}$ haloalkoxy, nitro and —S(O)$_z$CH$_3$;

a is one or two, where a is two the groups (CR$^{24}$R$^{25}$) may be the same or different;

an enolic tautomeric form thereof, or an agriculturally acceptable salt or metal complex thereof.

18. A method according to claim 17 in which the compound of formula (II) has one or more of the following features:

$R^{11}$ is hydrogen and X is oxygen;

$R^{12}$, $R^{13}$, $R^{16}$ and $R^{17}$ each represent hydrogen, and $R^{14}$ and $R^{15}$ independently represent hydrogen or methyl;

$R^{18}$ is halogen or nitro;

$R^{19}$ is $C_{1-4}$ alkoxy or —S(O)$_z$R$^{23}$ or —OSO$_2$R$^{23}$, where $R^{23}$ is $C_{1-4}$ alkyl;

e is one or two.

19. A method according to claim 18 in which either e is one and $R^{19}$ occupies the 4-position of the benzoyl ring; or e is two and the two groups $R^{19}$ occupy the 3- and 4-positions of the benzoyl ring.

20. A method according to claim 19 in which the compound of formula (II) is 2-(2-chloro-4-methylsulfonylbenzoyl)cyclohexane-1,3-dione; 2-(2'-nitro-4'-methylsulfonylbenzoyl)cyclohexane-1,3-dione; 2-(2'-nitro-4'-methylsulfonylexybenzoyl)cyclohexane-1,3-dione; 2-cyano-1-(4-methylsulphonyl-2-trifluoromethylphenyl)-3-(1-methylcyclopropyl)propan-1,3-dione; or 2-(2'-chloro-3-ethoxy-4'-ethylsulfonylbenzoyl)-4-methylcyclohexane-1,3-dione.

21. A method according to claim 2 in which the HPPD-inhibiting herbicide is a 2-cyano-1,3-dione herbicide having the general formula (III):

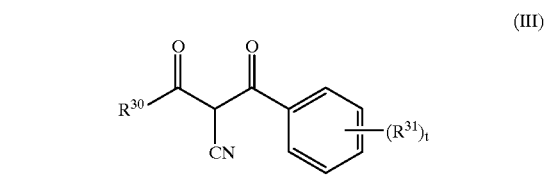

wherein $R^{30}$ is $C_{1-4}$ alkyl or $C_{3-6}$ cycloalkyl optionally substituted by $C_{1-6}$ alkyl;

$R^{31}$ is selected from halogen, nitro, cyano, —S(O)$_r$R$^{32}$, —(CR$^{33}$R$^{34}$)$_v$S(O)$_r$R$^{32}$, —N(R$^{35}$)SO$_2$R$^{32}$, $C_{1-6}$ alkoxy, —OSO$_2$R$^{32}$, $C_{1-4}$ haloalkoxy, $C_{1-4}$ alkyl and $C_{1-4}$ haloalkyl;

or two groups $R^{31}$, on adjacent carbon atoms of the phenyl ring may, together with the carbon atoms to which they are attached, form a 5 or 6 membered saturated or unsaturated heterocyclic ring containing up to three ring heteroatoms selected from nitrogen, oxygen and sulfur, which ring may be optionally substituted by one or more groups selected from halogen, nitro, —S(O)$_r$R$^{32}$, $C_{1-4}$ alkyl, $C_{1-4}$ alkoxy, $C_{1-4}$ haloalkyl and $C_{1-4}$ haloalkoxy, it being understood that a sulphur atom, where present in the ring, may be in the form of a group —SO— or —SO$_2$— t is an integer from one to five;

r is zero, one or two;

$R^{32}$ is $C_{1-4}$ alkyl, or phenyl or benzyl, each of phenyl and benzyl optionally bearing from one to five substituents which may be the same or different selected from the group consisting of halogen, $C_{1-4}$ alkyl, $C_{1-4}$ alkoxy, $C_{1-4}$ haloalkyl, $C_{1-4}$ haloalkoxy, nitro and —S(O)$_r$CH$_3$;

$R^{33}$, $R^{34}$ and $R^{35}$ are independently hydrogen or $C_{1-4}$ alkyl;

v is zero, one or two; where v is two the groups (CR$^{33}$R$^{34}$) may be the same or different v is one or two;

an enolic tautomeric form thereof, or an agriculturally acceptable salt or metal complex thereof.

22. A method according to claim 21 having one or more of the following features:

$R^{30}$ is 1-methylcyclopropyl or cyclopropyl;

$R^{31}$ is selected from halogen, —S(O)$_r$Me, trifluoromethyl, $C_{1-4}$ haloalkoxy, $C_{1-4}$ alkoxy and —CH$_2$S(O)$_r$Me;

t is one, two or three;

and one of the groups $R^{31}$ is —S(O)$_r$Me.

23. A method according to claim 22 in which the compound of formula (III) is 3-cyclopropyl-2-cyano-1-(2-methylsulphonyl-4-trifluoromethylphenyl)propan-1,3-dione; 1-(2-chloro-4-methylsulphonylphenyl)-2-cyano-3-cyclopropylpropan-1,3-dione; 2-cyano-3-cyclopropyl-1-(4-fluoro-3-methoxy-2-methylsulphonylphenyl)propan-1,3-dione; or 1-(4-chloro-2-methylsulphonylphenyl)-2-cyano-3-cyclopropylpropan-1,3-dione.

24. A method according to claim 1 wherein said application is early post-emergence.

* * * * *